United States Patent [19]

Jacques

[11] 4,454,345

[45] Jun. 12, 1984

[54] PROCESS FOR PREPARING 2,5-DICHLORO-3-NITROBENZOIC ACID

[75] Inventor: Albert M. V. Jacques, Philadelphia, Pa.

[73] Assignee: Union Carbide Corporation, Danbury, Conn.

[21] Appl. No.: 79,645

[22] Filed: Sep. 27, 1979

[51] Int. Cl.$^3$ ............................................ C07C 51/16
[52] U.S. Cl. ................................................... 562/410
[58] Field of Search .......................................... 562/410

[56] References Cited

U.S. PATENT DOCUMENTS 2,815,373  12/1957  Mayurnik ............................. 562/410
3,037,054   5/1962  DiBella ................................ 562/410
3,235,587   2/1966  Boffa et al. .......................... 562/410

*Primary Examiner*—Alan Siegel
*Attorney, Agent, or Firm*—D. L. Carlson; G. L. Coon

[57] ABSTRACT

The invention relates to a process of preparing 2,5-dichloro-3-nitrobenzoic acid by reacting 1,4-dimethyl-2,5-dichloro-3-nitrobenzene with aqueous nitric acid.

7 Claims, No Drawings

PROCESS FOR PREPARING 2,5-DICHLORO-3-NITROBENZOIC ACID

BACKGROUND OF THE INVENTION

This invention relates to an improved process for preparing 2,5-dichloro-3-nitorbenzoic acid. This acid and processes for its preparation are well known to those of skill in the art. It is an important compound because of its herbicidal activity itself and because of its utility as an intermediate in the preparation of 2,5-dichloro-3-aminobenzoic acid, another important herbicidally active compound. The herbicidal activity of 2,5-dichloro-3-nitrobenzoic acid and its functional derivatives is described in U.S. Pat. No. 3,013,873, and the herbicidal activity of 2,5-dichloro-3-aminobenzoic acid, its functional derivatives and their preparation from the 3-nitro compounds are described in U.S. Nos. 3,014,063 and 3,174,842.

Heretofore, a widely used procedure for preparing 2,5-dichloro-3-nitrobenzoic acid involved the nitration of 2,5-dichlorobenzoic acid. While this procedure yields the desired 3-nitro compound it suffers from a number of inherent disadvantages. For example, this procedure results in the production of a significant amount of the corresponding 6-nitro compound as a by-product.

The separation of the unwanted 6-nitro isomer from the desired 3-nitro compound is extremely difficult and requires the use of elaborate and cumbersome purification procedures which result in low yields of the desired 3-nitro compound. Consequently, there exists a need for a more effective process for preparing 2,5-dichloro-3-nitrobenzoic acid in increased yields that avoids the need to resort to elaborate and cumbersome purification techniques.

SUMMARY OF THE INVENTION

According to the present invention there is provided an improved method for preparing 2,5-dichloro-3-nitrobenzoic acid in high purity and good yields from 1,4-dimethyl-2,5-dichloro-3-nitrobenzene.

DETAILED DESCRIPTON OF THE PREFERRED EMBODIMENTS

This invention is directed to a method of preparing 2,5-dichloro-3-nitrobenzoic acid which comprises reacting a compound of the formula:

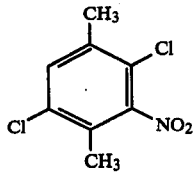

with aqueous nitric acid.

The 1,4-dimethyl-2,5-dichloro-3-nitrobenzene employed as the reactant in the process of this invention is a known compound that can be prepared by conventional methods. For example, this compound can be prepared by any of the methods of aromatic chlorination and nitration normally employed in organic chemistry. By way of illustration, 1,4-dimethylbenzene can be treated with chlorine gas in the presence of iron or ferric chloride to produce the chlorinated product, and this chlorinated product can, in turn, be nitrated using nitric acid to produce 1,4-dimethyl-2,5-dichloro-3-nitrobenzene. The 1,4-dimethyl benzene compound used as a precursor in the preparation of the 1,4-dimethyl-2,5-dichloro-3-nitrobenzene reactant can be readily obtained from commercial sources or prepared by known procedures.

The process is carried out by treating 1,4-dimethyl-2,5-dichloro-3-nitrobenzene with a quantity of a mixture of water and nitric acid sufficient to produce 2,5-dichloro-3-nitrobenzoic acid. In the preferred embodiment of this invention the quantity of the mixture employed in the preferred embodiments of this reaction is from about 85 to about 99 weight percent based on the total weight of the reaction mixture. The quantity of the mixture preferred in the particularly preferred embodiment of this invention is from about 90 to about 98 weight percent based on the total weight of the reaction mixture.

The mixture contains as its essential components nitric acid and water. Preferably, the mixture contains from about 10 to about 50 weight percent nitric acid based on the total weight of nitric acid and water in said mixture. In the particularly preferred embodiment of this invention, the mixture contains from about 15 to about 30 weight percent nitric acid based on the total weight of nitric acid and water.

Preferably, the mixture of nitric acid and water is premixed prior to reaction with 1,4-dimethyl-2,5-dichloro-3-nitrobenzene. Alternatively, the nitric acid and water can be added to the 1,4-dimethyl-2,5-dichloro-3-nitrobenzene stepwise in any sequential order.

Reaction temperatures are not critical. Reaction temperatures can vary from about 150° C. to the degradation temperature of the reactants and products. In the preferred embodiment of this invention, the reaction temperature can vary from about 150° C. to about 210° C. In the particularly preferred embodiment of this invention, the process is conducted at a temperature of from about 160 to about 200° C.

Reaction pressures are not critical. A closed reactor is required in order to achieve the necessary reaction temperature. Preferably, the reaction is conducted at autogenous pressure.

The process of this invention is carried out for a period of time sufficient to produce the desired 2,5-dichloro-3-nitrobenzoic acid compound. It should be appreciated that the reaction time will be influenced to a significant extent by the reactants; the reaction temperature and by other factors known to those of skill in the art. In general, residence times can vary from about a few minutes to 24 hours or longer. In most instances, when employing preferred reaction conditions, reaction times will be found to vary from about 1 to about 5 hours.

The process of this invention can be conducted in a batch, semi-continuous or continuous fashion. The process can be conducted in a single reaction zone or in a plurality of reaction zones, in series or in parallel or the process may be conducted intermittently or continuously in an elongated zone or series of such zones. The materials of construction employed should be inert to the reactants during the reaction and the fabrication of the equipment should be able to withstand the reaction temperatures and reaction pressures.

The reaction zone can be fitted with one or more internal or external heat exchanger(s) in order to heat the reaction mass; control undue temperature fluctuation or to prevent any possible "runaway" reaction temperatures. In the preferred embodiment of the process of this invention, agitation means to mix the reaction mixture can be employed, preferably using a stirrer such as a motor driven impeller.

The reactants and reagents may be initially introduced into the reaction zone batchwise or they may be continuously or intermittently introduced into such zone during the course of the process. Means to introduce or to adjust the quantity of reactants introduced either intermittently or continuously into the reaction zone during the course of the reaction can be conveniently utilized in the process to maintain the desired ratioes of the reactants.

The following examples are presented to more specifically illustrate the process of this invention.

EXAMPLE I

To a 2-liter stainless steel autoclave was added 12.6 grams (0.057 moles) of 1,4-dimethyl-2,5-dichloro-3-nitrobenzene, 124 ml (1.98 moles) of 70.7% nitric acid and 376 ml of water. The resulting mixture was sealed in the autoclave using an "Inconel" rupture disk. The mixture was heated to 190° C., at which time the rupture disk on the reactor blew, resulting in a loss of most of the mixture. A portion of the mixture recovered from outside of the autoclave was dissolved in saturated NaHCO$_3$, filtered and reprecipitated using concentrated HCl to give 0.2 grams of pale tan powder. Gas-liquid chromatrography (hereinafter referred to as "GLC") analysis of the powder showed the composition to be 96 0 wt.% 2,5-dichloro-3-nitrobenzoic acid.

A portion of the mixture recovered from inside the autoclave was similarly treated to yield 0.7 grams of tan powder. GLC analysis of this powder showed the composition to be 96.0 wt.% 2,5-dichloro-3-nitrobenzoic acid. The acidic filtrates recovered after filtering the above 2,5-dichloro-3-nitrobenzoic acid precipitates were combined, flash evaporated to dryness and dissolved in acetone. The insoluble NaCL was filtered off and the acetone filtrate was evaporated to dryness to yield 0.5 grams of an impure water soluble acid. Infra red spectroscopy analysis of this acid showed it to be mainly 2,5-dichloro-3-nitroterephthalic acid.

EXAMPLE II

To a 2-liter stainless steel glass-lined autoclave was added 17.7 grams (0.08 moles) of 1,4-dimethyl-2,5-dichloro-3-nitrobenzene, 124 ml (1.98 moles) of 70.7% nitric acid and 376 ml of water. The resulting mixture was sealed in the autoclave using an SS.316 rupture disk. The mixture was stirred while heating to a temperature of 199° C. over 4½ hours. The mixture was then held at 200° C. for 3 hours and then cooled overnight.

After cooling, the contents of the autoclave were taken up in acetone, and filtered, and the resulting filtrate was flash evaporated to remove the acetone. At this point, solids developed in the residual aqueous phase after acetone removal. The solids were filtered, washed with water and dissolved in saturated NaHCO$_3$. The resulting solution was extracted twice with chloroform to remove any unoxidized or partially oxidized material, and the residual aqueous phase was acidified with concentrated HCl. The resulting precipitate was washed and dried to yield 7.1 grams of white solids. GLC analysis showed these white solids to contain 94.16 wt.% 2,5-dichloro-3-nitrobenzoic acid. The corresponding yield to 2,5-dichloro-3-nitrobenzoic acid was 35.41 percent.

COMPARISON

As a comparative example, materials identical to those of Example II were placed in a 2-liter stainless steel autoclave, sealed and heated with agitation 111° C. over 2 hours, followed by holding at an average of 109° C. over 5¾ hours. The product was worked up following the procedure of Example II and analyzed to contain no 2,5-dichloro-3-nitrobenzoic acid. Instead, 17 grams of 1,4-dimethyl-2,5-dichloro-3-nitrobenzene of 99.16 wt.% purity was recovered.

EXAMPLE III

Materials identical in kind and amount to those of Example II were placed in a glass-lined 2-liter stainless steel autoclave, sealed, stirred and heated to 180° C. over 3 hours and 20 minutes, followed by heating at 182° C. for 25 minutes.

After cooling, the product was worked up following the procedure of Example II to yield 10.3 grams of white solid which was analyzed by GLC to contain 79.8 wt.% 2,5-dichloro-3-nitrobenzoic acid.

The yield of 2,5-dichloro-3-nitrobenzoic acid was 43.5 percent based on GLC analysis.

EXAMPLE IV

Materials identical in kind and amount to those of Example II were placed in a 2-liter stainless steel autoclave, sealed, stirred and heated to 165° C. over 3 hours, followed by heating at 164° for 4½ hours.

After cooling, the crude product was treated in accordance with the procedure of Example II to yield 10.6 grams of cream solids analyzed by GLC to contain 74.3 wt.% 2,5-dichloro-3-nitrobenzoic acid and 2.3 wt.% 2,5-dichloro-3-nitroterephthalic acid.

The acidic filtrate recovered after filtration of the above 2,5-dichloro-3-nitrobenzoic acid was flashed evaporated to dryness, dissolved in acetone and filtered to remove NaCl. The filtrate was evaporated to dryness to yield 1.0 grams of khaki solids which by GLC analysis was shown to contain 19.05 wt.% 2,5-dichloro-3-nitrobenzoic acid and 40.18 wt.% of 2,5-dichloro-3-nitroterephthalic acid.

The yield of 2,5-dichloro-3-nitrobenzoic acid was 41.7 percent based on GLC analysis.

EXAMPLE V

A mixture 17.8 grams (0.08 moles) of 1,4-dimethyl-2,5-dichloro-3-nitrobenzene, 25 ml (0.399 moles) of 770.7% nitric acid, and 475 ml of water were sealed into a 2-liter stainless steel autoclave without a glass liner. The stirred mixture was heated to 162° C. over 4 hours, followed by heating at an average of 165° C. for 3¾ hours.

After cooling, the mixture was treated in accordance with the procedure of Example II to yield 1.8 grams of white solids which were shown by GLC analysis to contain 88.3 wt.% 2,5-dichloro-3-nitrobenzoic acid.

The resulting product was extracted with chloroform to form a chloroform phase. Upon flash evaporation of the product, there was obtained 13.9 grams of pale yellow solids, shown by GLC analysis to contain 95.86 wt.% of unreacted 1,4-dimethyl-2,5-dichloro-3-nitrobenzene.

The yield of 2,5-dichloro-3-nitrobenzoic acid was 8.4 percent based on the GLC analysis.

EXAMPLE VI

Materials identical to those of Example II were placed in a glass-lined 2-liter stainless steel autoclave, sealed stirred and heated to 159° C. over 3¾ hours, followed by heating at an average of 163.5° C. for 1½ hours.

After cooling, the crude product was treated in accordance with the procedure of Example II to yield 10.2 grams of off-white solids, analyzed by GLC to contan 80.1 wt.% 2,5-dichloro-3-nitrobenzoic acid.

The yield of 2,5-dichloro-3-nitrobenzoic acid was 43.3 percent based on GLC analysis.

EXAMPLE VII

Materials identical in kind and amount to those of Example II were placed in a glass-lined 2-liter stainless steel autoclave, sealed, stirred and heated to 197.5° C. over 3 hours and 10 minutes, followed by heating at an average of 202.5° C. for 18 minutes.

After cooling, the crude product was treated in accordance with the procedure of Example II to yield 7.5 grams of white powder, analyzed by GLC to contain 96.2 wt.% 2,5-dichloro-3-nitrobenzoic acid.

The yield of 2,5-dichloro-3-nitrobenzoic acid was 38.2 percent based on GLC analysis.

What is claimed is:

1. A method of preparing 2,5-dichloro-3-nitrobenzoic acid which comprises reacting 1,4-dimethyl-2,5-dichloro-3-nitrobenzene with aqueous nitric acid at a reaction temperature of at least about 150° C.

2. The method of claim 1 wherein the reaction temperature is between about 150° C. and about 210° C.

3. The method of claim 1 wherein the reaction temperature is between about 160° C. and about 200° C.

4. The method of claim 1 wherein the aqueous nitric acid comprises from about 10 to about 50 weight percent nitric acid based on the total amount of nitric acid and water in said aqueous nitric acid.

5. The method of claim 4 wherein the aqueous nitric acid comprises from about 15 to about 30 weight percent nitric acid based on the total amount of nitric acid and water in said aqueous nitric acid.

6. The method of claim 1 wherein the aqueous nitric acid is present in an amount of from about 85 to about 99 weight percent based upon the total weight of said aqueous nitric acid plus said 1,4-dimethyl-2,5-dichloro-3-nitrobenzene.

7. The method of claim 6 wherein the aqueous nitric acid is present in an amount of from about 90 to about 98 weight percent based upon the total weight of said aqueous nitric acid plus said 1,4-dimethyl-2,5-dichloro-3nitrobenzene.

* * * * *